United States Patent [19]

Steuart et al.

[11] Patent Number: 5,330,756
[45] Date of Patent: Jul. 19, 1994

[54] POLYPHASE FLUID EXTRACTION PROCESS, RESULTING PRODUCTS AND METHODS OF USE

[76] Inventors: Gary M. Steuart, 98 Viking Terr., Northfield, Minn. 55057; M. Conrad Huffstutler, Jr., 6200 Lynn La., Lago Vista, Tex. 78645

[21] Appl. No.: 980,839

[22] Filed: Nov. 24, 1992

Related U.S. Application Data

[63] Continuation-in-part of Ser. No. 599,616, Oct. 18, 1990, abandoned.

[51] Int. Cl.⁵ .................... A01N 25/02; A01N 65/00; A61K 35/78; A61K 37/22
[52] U.S. Cl. ........................................ 424/405; 424/43; 424/44; 424/45; 424/450; 424/47; 424/195.1; 424/401; 424/DIG. 15; 514/937; 514/965; 436/829
[58] Field of Search ................ 424/401, 405, 450, 43, 424/44, 45, 46, 47, 195.1, 443, 433, DIG. 15, 937; 514/965; 264/4; 436/829

[56] References Cited

U.S. PATENT DOCUMENTS 4,670,263 6/1987 Noorlander ...................... 424/195.1

OTHER PUBLICATIONS

*Phytoalexins* pp. 519-521, vol. 13, McGraw Hill Encyclopedia of Science and Technology, 7th Ed., 1992.
*Chemotaxonomy* pp. 545-549 ibid.

Primary Examiner—Thurman K. Page
Assistant Examiner—Carlos Azpuru
Attorney, Agent, or Firm—M. Conrad Huffstutler, Jr.

[57] ABSTRACT

Processes for polyphase fluid extraction of concentrated, active therapeutic components from parts of plants identified taxonomically as Symphytum, Taxus and Aloe species are described. The resulting products-by-processes are defined as Concentrated Fluid Plant Extracts (CFPE) of the respective plant types, where P can be S, T or A. The preparation process for CFPE includes multiple/sequential stages of diffusional transfer of the active constituents into liquid and/or vapor extraction phases under contact conditions of forced convection at controlled temperature and pressure. Therapeutic formulations based on CFPE including emulsions, aerosols, liposomes and controlled-release devices are presented. Treatment methods for a variety of skin conditions and complications of specific diseases are indicated.

5 Claims, No Drawings

POLYPHASE FLUID EXTRACTION PROCESS, RESULTING PRODUCTS AND METHODS OF USE

RELATED APPLICATION

This application is a continuation-in-part of Ser. No. 07/599,616, filed Oct. 18, 1990, now abandoned.

BACKGROUND OF THE INVENTION

Technical Field

This invention relates to medicaments containing Concentrated fluid (CF) Extracts of Plant species taxonomically identified as Symphytum, Aloe or Taxus, processes for their preparation in various forms and methods for use of the several medicaments and fore for therapy on humans and other mammals.

GENERAL BACKGROUND

A. CF Symphytum Extracts

Alcohol or glycol extract solutions of plants reported to be *S. officinale*, which is called "comfrey" in English, are well known as wound-healing agents as used in topical preparations. Typically, dried "comfrey" roots/leaves are extracted at room temperature in solvents such as ethanol and the resulting solution will contain at least trace amounts of some of the known medicinal agents including allantoin, asparagine, and mucoplysaccharides. As with all medicinal or herbal plants, the actual chemical constituents of in-vivo plant parts are highly dependent upon the maturity at harvest, available soil moisture and nutients, and environmental factors such as pollution, climate parameters such as growth-season degree days and freedom from disease and insect infestation. Classic herbal medicine references do not have any definite values for the actual level of identified active components in the resulting extracts, or indications as to the probability of dangerous impurities and contaminants which may also be present. This continuing lack of specificity concerning how to grow and harvest selected plant types, what plant parts to extract, how to do the extraction to get optimal or efficient therapeutic concentration is no doubt responsible for the various "comfrey" controversies such as poisoning of humans and animals due to pyrrolizidine alkloids. For products marketed in USA, the FDA has determined that no therapeutic claims can be made for any old-type "comfrey" compositions which have not been subjected to comprehensive lab-/animal/and clinical validations according to detailed IND and NDA procedures.

It has long been desired to develop topical compounds with concentrated levels of healing extract that are high enough to give a distinct healing response to skin or mucous membranes while at the same time having skin moisturizing properties. The "ideal" product should have an extended shelf life e.g., 9 months to 2 years. Further, it is desirable that the product does not create skin irritation i.e., a burning sensation on an open wound such as occurs with alcohol or propylene glycol preparations containing "comfrey".

"Comfrey" has been recognized for decades for its healing properties, particularly for its ability to stimulate epithelial development externally in the case of skin damage or breakdown and internally in the case of stomach ulcers. Original applications were using a "comfrey" tea made by boiling the leaves and stems or the roots in liquid water for a short time. The filtered liquid-solution product, tea, was taken orally for various medical symptoms or it could be applied externally to the skin surface. MacAllister (1902) reports that poultices were made by mashing or grinding fresh "comfrey" leaves or roots and applying the resulting fibrous slurry directly to wounds to stimulate healing. Alcohol tinctures were made by using pure liquid alcohol as defined by the U.S. Pharmacopeia and water to extract the healing properties from "comfrey" roots. After filtration to remove the solids, that tincture was used for external applications to promote healing. Homeopathic Pharmacopeia (1978) describes a typical preparation method based upon dissolved "comfrey" extracts. No patent or research publication could be found which describes extraction of "comfrey" by fluids other than single-phase, single-component liquids.

U.S. Pat. No. 3,930,000 teaches that solvent extracts of the roots of plants reported to be "comfrey" contain a natural predecessor of synthetic allantoin which is known as 5-ureidohydantoin in the chemical literature. U.S. Pat. No. 4,670,263 discloses ointments containing stem and leaf extracts, using filtered propylene glycol, of "comfrey", along with additives including synthetic allantoin, ascorbic acid, chlorophyll, carotene and lanolin which are claimed to be effective for treating bovine mastitis and bovine metritis. The teaching states that either "green" or "dried" plant parts may be extracted with aqueous propylene glycol solutions to produce "comfrey ointments" based upon mixing "comfrey extracts in propylene glycol" with oily ointment-bases such as mineral oil and lanolin. The specification is silent on the question of micronutrients/trace minerals which must be present in the soil and any preferred horticultural procedures (average daytime sunlight intensity, growth-season degree days, average soil temperature, timing of harvest in growth season, soil and air moisture, soil nutrients, etc.). The specification does not teach any method of selecting plants according to maturity, health/freedom from plant diseases, or contamination/freedom from residues of agricultural chemicals such as herbicides, pesticides. Curiously, the specification does not mention the known carcinogenicity/hepatotoxicity of pyrrolzidine alkaloids derived from "comfrey". Neither does the specification mention the known tendancy of PG (propylene glycol) topical-pharmaceutical vehicles to produce skin sensitization, eczema, skin irritations and allergies when present in concentrations exceeding the isotonic concentration of 2%.

These "comfrey propylene glycol extracts" appear to be defined by the process of soaking from 283–681 grams of "green comfrey plant" in about 3931 grams of liquid propylene glycol (PG); after "filtration" to remove suspended solid matter and the coarse fibrous material, the filtrate solution is then further diluted with about 421–3459 grams of water. The teaching indicates that the PG solution may be heated to 99 deg. C. to "increase the rate of extraction"; however, no specific extraction time is given. Because no data are given for the weight of solids separated by the "filtration" step of the technique, it is impossible to calculate the actual resulting level of "comfrey extract" dissolved and/or dispersed in either the propylene-glycol stage or the final-dilution stage. By analogy with other extracts from plant tissue, it is estimated that the active "comfrey components" extracted by typical practice amounts to approximately 0.01 to 0.02 wt. % of the final diluted preparation. U.S. Pat. No. 4,847,084 discloses two ointments for treatment of decubitus ulcers, Decubitane #1 and #2, which are based upon a debriding enzyme, fibrinolysin, with additives including chlorophyll and povidoneiodine. U.S. Pat. No. 3,622,668 discloses a scar-inhibiting lotion for treatment of livestock injuries which contains phenol, retinol, ergosterol and olive oil, or fish oil. None of the disclosed or claimed "comfrey" treatment formulations for humans or other mammals are foams, controlled-release particles, controlled-release implants, emulsions, vesicles, liposomes, aerosols or micelles.

Several commercial sources offer "comfrey-containing" topical ointments e.g., human or veterinary grades, for treatment of skin irritations, rashes and minor wounds. These consist of "comfrey" liquid ethanol extracts mixed with an oily base. These oily bases typically contain various oils including almond and other vegetable oils blended with beeswax. Any suspensions or slurries present in these products appear to be stable against separation upon shelf storage at room temperature at least for a short time.

Commercial products that are labeled as containing "comfrey" extract appear to have variable "comfrey" contents below 0.01 wt. %. Generally, commercial "comfrey"-containing products are comprised of formulas with the base having over 50 wt. % wax and oil, high levels of propylene glycol, and/or high levels of alcohol. No evidence can be found of a true O/W emulsion with either consistent or high levels of "non-water comfrey components" in the final formulation i.e., greater than 0.02 wt. %.

In order to evaluate the characteristics of propyleneglycol-based "comfrey" extracts with 25-75 vol. % propylene glycol, experimental solution-type topical formulations were prepared and applied to various kinds of human skin injuries and diseases. Although these extracts exhibited healing properties on epithelial tissue, their use often produced an undesirable skin irritation and burning sensation on an open wound or sensitive skin areas.

One outgrowth of the experimentation was the development of a preparation which consisted of a dispersion of an aqueous phase into an oil-based phase, i.e., a W/O or water-in-oil emulsion. The dispersed, water-solution phase consisted of 75 vol. % propylene glycol, balance water and "comfrey" extracts. The continuous oil phase was made of mineral oil and lanolin. "Comfrey" components made up 0.004-0.01 wt. % of the resulting formulation. This emulsion proved to be unstable upon shelf storage at room temperature.

After extensive experimentation with processing variables, a stable W/O emulsion was prepared that contained about 0.01 wt. % Symphytum components in the dispersed propylene glycol solution phase and a blend of beeswax, lanolin, and vegetable oil in the continuous oil phase.

B. CF Taxus Extracts

Taxines, baccatins, and taxol are the principal medicinal constituents which can be extracted from components of species identified taxonomically as *T. baccata, T. brevifolia, T. canadensis, T. chinesis, T. cuspidata, T. floridana* and other wild or non-wild types. Extractable plant elements include flowers, seeds, needles, leaves, buds, nuts, cones, blooms, branches, stems, bark and roots. The alkaloids in extracts are poisonous to humans and animals if taken internally; typical symptoms include GI irritation, and failure of circulatory and respiratory functions. Experimental parenteral "taxol" preparations (developed by chemical modification and synthesis) are believed to be useful, along with other known radiation and chemotherapy technics, for treatment of certain tumors. Bitter disputes between EPA and several environmental groups have essentially halted scientific progress in this field in USA.

No publications on: (a) poly-phase, fluid-extraction processes or (b) fine-disperse mammalian therapeutic forms can be found for extracts of plant parts of any Taxus-type plant.

C. CF Aloe Extracts

Aloin, is the principal medicinal constituent of thickened, leaf-cell fluid of species identified taxonomically as *A. perryi*, or *A. vera* and other wild or non-wild types; the other constituents include resin, emodin and a mixture of volatile oils. Extractable plant components include flowers, seeds, leaves, anthers, buds, blooms, stems and roots. Aloin isolates administered orally are known for cathartic and purgative use. According to the lore of herbal medicine, "aloe extacts" are useful for skin care and moisturization.

No publications on: (a) poly-phase, fluid-extraction processes or (b) fine-disperse mammalian therapeutic forms can be found for extracts of plant parts of any Aloe-type plant.

SUMMARY OF THE INVENTION

The main object of this invention is the preparation of Concentrated Fluid Symphytum Extracts (CFSE) are prepared for therapeutic use by means of single or polyphase extraction in a dosed, controlled environment from comminuted Symphytum plant matter. Single phase extraction means that a fluid in liquid or gas phase will be in contact with the plant parts to be extracted. Polyphase extraction means more than one phase of an extract fluid will be present in the environment, either simultaneously or chronologically, i.e., sequentially by the condensation of a vapor phase to produce a liquid phase. For the purpose of this specification and claims, CFSE are defined as those organic and inorganic constituents which are: (a) present in either fresh or air-dried plant matter, including at least one of the plant elements comprising flowers, seeds, leaves, anthers, buds, blooms, stems and roots, of any one or more wild or non-wild Symphytum species including *S. officinale, S. asperum, S. armeniacum, S. tauricum, S. sylvaticum, S. peregrinum, S. anatolicum, S. icaricum, S. orientale, S. kurdicum, S. pseudobulbosum, S. uplandicum, S. circinale, S. ottomanum, S. icaricum, S. brachycalyx, S. aintabicum, S. longisetum, S. bornmuelleri, S. tuberosum, S. bulbosum, S. ibericum,* or *S. longipetiolatum*, harvested at a mature stage i.e., peri-bloom, and (b) can be extracted in a controlled or recirculated environment with fluids in either a liquid or vapor state from whole parts or comminuted particles of any or all of the above-named plant elements at temperatures in the range of 15-110 deg. C. with an extractant-fluid contact interval of 1 to 200 hours and with starting input weight ratios of extract fluid/plant matter of 0.01/1 up to 10000/1. According to this definition, the fluid may be initially a vapor phase which permeates into the plant elements and will under equilibrium conditions and then nucleate and condense a liquid phase on and within the plant elements. Further, according to this invention the fluid may initially contain medical-type surfactants which enhance its capillary flow within the structure of the plant matter. Further according to this definition, the types of defined contact between the plant elements and the extracting fluid include gravity flow of a liquid condensate, gravity drainage of a liquid fluid sprayed from the upper zones of the reactor, circulation/fluidization by means of vapor phase with or without a dispersed equilibrium aerosol and forced convection circulation/fluidization by means of a liquid fluid. For such flow variations, the forced-convection-contact-velocity differential would fall in the range 0.01 to 10 meters/sec. Still further according to this definition, the defined extraction environment includes inert gases and/or condensable vapor phases in the range of pressures from 1 to 10000 kPa.

Another general object of the present invention is to provide new, improved therapeutic formulations and compositions of CFSE which can be used for dermatological treatment of a number of skin and mucosal membrane conditions in humans and animals. These conditions include but are not limited to: skin dryness/allergies/rashes, tissue healing, prevention of scaring complications, fungal infections, treatment of minor burns, etc.

The invention includes various physical forms of the CFSE formulations (emulsions, liposomes, aerosols) which are not available commercially or reported in the scientific literature. It is believed that the bioavailability of CFSE is enhanced in fine-dispersed forms relative to typical bulk-solution forms.

The invention includes therapeutic and dermatological formulations in various physical forms with high concentration levels of CFSE e.g., higher than any known "comfrey" preparations or published "comfrey" treatment protocols. Liquid preparations according to this invention contain CFSE components in excess of 0.02 wt. % of the total weight of the final preparation as used. The use of such enriched formulations according to this invention, thus allows smaller quantities of the preparation to be used to deliver the same amount of active components of the Symphytum extract.

For emulsion-type formulations, this invention includes topical CFSE consisting of O/W emulsions, oil being the dispersed phase and water the continuous phase, for the purpose of protecting, moisturizing, and stimulating the healing processes of skin or mucous membrane.

Skin-treatment O/W emulsion formulations according to this invention contain selected oils for moisturizing the skin, especially the stratum corneum and high levels of CFSE in the water phase for maximal healing properties.

This invention also includes improved methods for use of CFSE formulations in alternative physical forms including liquid emulsions such as foam, spray, gel, lotion, cream, ointment, and dispersed vesicles, particles or droplets solid- or liquid-aerosols, liposomes, microemulsions, for maximum effectiveness in wound healing.

This invention includes new methods for controlled-release of CFSE impregnated into a fibrous matrix or blended with an adhesive.

Patients with AIDS usually experience skin breakdown problems, e.g., folliculitis, "itchy red bumps", psoriasis, and dry itchy skin. Topical emulsion preparations of CFSE according to this invention significantly relieve the itching in many cases and help promote healthier skin.

Healthcare workers—because of frequent hand washing and wearing surgical gloves—often experience dermatitis, i.e., severe chapping and dryness of the skin.

Topical emulsion-type CFSE formulations according to this invention reduce dryness and, in many cases, stimulate healing to point that the skin becomes healthy again. Similarly, workers who are exposed to irritating substances in their occupation can use similar CFSE/formulations for either therapeutic or prophylactic purposes.

Diabetic patients often experience dry skin and in some cases stasis ulcers which heal with difficulty. Topical emulsion-type CFSE formulations according to this invention help relieve the dryness and in some cases has proven to be a good healing agent for the stasis ulcers.

Paraplegics or bedridden patients can experience pressure sores or decubitus ulcers. Topical emulsion-type CFSE formulations according to this invention help condition the skin and thus prevent the formation of the ulcers. Further, the formulations will stimulate the healing of those ulcers already extant.

Other uses for emulsion-type CFSE formulations according to this invention include: diaper rash, chapped or dry skin, sunburn, insect bites, minor wounds, cold sores, athlete's foot, and minor burns.

A secondary objective of this invention is the preparation and use of therapeutic compositions containing CF Taxus Extracts (CFTE) for treatment various forms of malignant disorders, cell-proliferative diseases and carcinomas. Specific extraction processing parameters fall in the ranges noted above for CFSE. This invention also includes improved methods for use of CFTE formulations in alternative physical forms including liquid emulsions, foam, spray, gel, lotion, cream, ointment, and dispersed vesicles, particles or droplets solid- or liquid-aerosols, liposomes, microemulsions, for maximum effectiveness in treatment of carcinomas, cell-proliferative diseases and malignant disorders. This invention includes new methods for controlled-release of CFTE impregnated into a porous/fibrous matrix or blended with an adhesive.

A tertiary objective of this invention is the preparation and use of therapeutic compositions containing CF Aloe Extracts (CFAE) for skin injuries/burns, inflammations, infections, and diseases. Specific extraction processing parameters fall in the ranges noted above for CFSE. This invention also includes improved methods for use of CFAE formulations in alternative physical forms including liquid emulsions, foam, spray, gel, lotion, cream, ointment, and dispersed vesicles, particles or droplets solid- or liquid-aerosols, liposomes, microemulsions, for maximum effectiveness in treatment of skin diseases, injuries, inflammations, and allergies/sensitizations. This invention includes new methods for controlled-release of CFAE impregnated into a porous/fibrous matrix or blended with an adhesive.

MODES FOR CARRYING OUT INVENTION

One preferred formulation of this invention is an O/W emulsion with at least 0.02 wt. % of active components within CFSE prepared as described in the following.

CF Symphytum Extract preparation. Preferably, fresh Symphytum leaves/stems or roots are used, and at least 12 grams of roots or 60 grams of leaves/stems are comminuted into one liter of liquid aqueous extracting fluid. Alternatively CF Symphytum Extract is made by comminuting at least 6 grams of dried Symphytum leaves and stems or dried roots and combining it with one liter of liquid aqueous extracting fluid. In this context, "dried" denotes less than 10 wt. % water, on an absolute or "bone-dry" basis. The forced-convection-contact-velocity differential for the process should be in the range 0.01 to 10 meter/sec.

For another preferred embodiment, the extracting fluid may be an undiluted or "neat" liquid such as propylene glycol, glycerol, ethyl alcohol, water, methylene chloride and the chamber environment is the vapor of the liquid at a pressure of about 100 kPa. Alternatively, the extract fluid may be a liquid solution or two-phase emulsion. The extraction process requires approximately 72 hours contact at temperatures between 20 and 30 deg. C. The forced-convection-contact-velocity differential for the process should be in the range 0.01 to 10 meter/sec. The supernatant extract is filtered thru typical food-type paper filters (nominal pore size 10-100 micrometers).

In the case of extraction with a physiologically-compatible solution (generally isotonic to blood and tissue, 250-350 mOsm/kg), the filtrate may be used directly to prepare final liquid formulations for use in intravenous, subcutaneous, intramuscular, intralymphatic, intraperitoneal, or intraplueral preparations.

Alternatively, the filtrate may be evaporated to reduce the extractant to as little as zero %. To facilitate preparation of certain formulations or physical forms, the extraction step can be done with water or aqueous solutions containing a reduced level of physiologic components (such as saline) and the final adjustment to physiologic osmolality range being accomplished by addition of specific concentrates to the filtered CF Symphytum Extract.

The concentrated filtrate can be added directly to the water phase or it can be re-suspended with an alternative vehicle, e.g. water, glycerol, propylene glycol. One kilogram of the final formulation contains CF Symphytum Extract from at least 6 grams of dried leaves and stems or roots, or the extract from at least 60 grams of fresh leaves/stems or the extract from at least 12 grams of fresh roots.

In typical O/W emulsions, the volume percent of the dispersed phase is in the range of 0.1-25 vol. %. For these formulations, the major quantity of CF Symphytum Extract is contained in the water-solution phase of the emulsion, whether it is a simple O/W emulsion or a complex W/O/W emulsion wherein water is the continuous phase and the primary dispersed phase is oil droplets which in turn contain smaller droplets of the continuous phase, water. W/O/W dispersions may also be called double or multiple emulsions.

Liposome dispersions of CFSE can be made spontaneously by the technique of adding a quantity of aqueous extract solution to a dry film of lipid or phospholipid. Other known alternative methods of forming liposomes such as injection, reverse-micelle formation and reverse-phase evaporation can also be used to produce liposomes from aqueous CFSE. The therapeutic characteristics of the resulting vesicles can be tailored for specific diseases or tissue applications by: (a) altering the average diameter/size of the vesicle, (b) altering the surface charge of the vesicle, (c) altering the stiffness of the encapsulating vesicle membrane-film and (d) incorporation of antibodies or ligands into the vesicle surface/film which show binding or affinity for specific types/forms of tissue.

Aerosol dispersions of solid- or liquid-phase CFSE can be made by techniques such as atomization, nebulization, spray drying, freeze drying.

CFTE Extraction Technics fluid type: water, C1-C10 alcohols, C1-C3 ketones, C1-C4 acetates, C1-C4 ethers, C1-C3 halocarbons, and solutions/dispersions thereof in liquid and/or vapor phases pressure range: 0.1X<vapor pressure of most-volatile fluid component at maximum extraction temperature in cycle, deg. C.<20X temperature range: 15-110 deg. C.

mass-transport parameters: 0.01/1<weight ratio input plant parts/extract<10000/1 0.01<forced-convection-contact-velocity differential, meter/sec<10 total diffusional contact time: 1<cycle time, hours<200

CFTE Formulations and Use Technics

A wide variety of CFTE formulations can be made; these include topical, transdermal, transmucosal, parenteral compositions in fluid-forms i.e., solutions, suspensions, emulsions, and fine-disperse forms such as foams, liposomes, vesicles, micelles and aerosols. Known pharmaceutical excipients appropriate to the specific administration mode and use-form can be blended with CFTE. For therapy of carcinomas and malignant disorders, parenteral forms of CFTE can be used; however, targeted liposome formulations adapted for breast or uterine tumor treatment are preferred.

CFAE Extraction Technics fluid type: water, C1-C10 alcohols, C1-C3 ketones, C1-C4 acetates, C1-C4 ethers, C1-C3 halocarbons, and solutions/dispersions thereof in liquid and/or vapor phases pressure range: 0.1X<vapor pressure of most-volatile fluid component at maximum extraction temperature in cycle, kPa at max. temp deg. C.<20X temperature range: 15-110 deg. C.

mass-transport parameters: 0.01/1<weight ratio input plant parts/extract<10000/1 0.01<forced-convection-contact-velocity differential, meter/sec<10 total diffusional contact time: 1<cycle time, hours<200

CFAE Therapeutic Formulations and Use Technics

A wide variety of CFAE formulations can be made; these include topical, transdermal, transmucosal, parenteral compositions in fluid-forms i.e., solutions, suspensions, emulsions, and fine-disperse forms such as foams, liposomes, vesicles, micelles and aerosols. Known pharmaceutical excipients appropriate to the specific administration mode and use-form can be blended with CFAE.

EXAMPLES

Group A. Examples of processes for: (a) preparation of the Symphytum plant materials to be extracted and (b) the preparation including refining (filtration/concentration/purification) of CFSE.

Example A1. Peri-Harvest Treatment Protocol 1012

This is a process of peri-harvest conditioning/treatment/handling of the plant materials i.e., leaves, stems and/or roots, of Symphytum species which preserves their medicinal agents against evaporation, chemical degradation and photochemical interactions in the time interval between harvest and initiation of the extraction contact including the steps of:

(a) by visual inspection and other chemical/microbiological tests, selecting zones of the production field which contain Symphytum plants which have reached an optimum level of maturity (peri-bloom stage) and are essentially free of disease and have no significant levels of undesirable materials/bacteria (e.g., pyrrolozidine alkaloids) or adventitious contaminants, (b) treating selected zones of plants to be harvested with solutions containing for example viable *Lactobacillus planterum* which can reduce the numbers of undesirable adventitious bacteria such as *E. coli* or Klebsiella, (c) charging the harvested plant materials immediately (within a time period of 10-50 minutes) into a closed collection apparatus which prevents exposure to sunlight, and (d) transferring the collected plant materials into specialized extraction apparatus for additional processing.

Example A2. Compression/Liquid-Fluid Extraction Process for Concentrating Symphytum Extracts This is a method of compacting/comminuting/extracting fresh plant materials of Symphytum species which includes the steps:

(a) receiving collected plant materials from an enclosed in-field collection/processing apparatus (see Example A1 above), (b) comminuting the plant materials to small pieces (avg. length or thickness dimension approx. 1 mm) by known processes such as chopping or macerating, (c) charging the comminuted plant material into a closed reactor adapted to provide controlled ranges of internal pressure, temperature and forced-convection-contact-velocity differential within a time interval of 2-6 hours after receipt, (d) charging the reactor with a liquid or liquid-mixture extracting fluid such as alcohol or water or propylene glycol or glycerol or mixtures of these components at a selected temperature in the range between 15-55 deg. C., (e) contacting the enclosed plant materials under sealed environmental conditions for a time of 2 to 100 hours, preferably 4-8 at a pressure of 50-200 kPa, with controlled mechanical agitation by means of blades, or a rotating/tumbling reactor chamber, and (f) treating the extract mixture (fluid and solids) by one or more mechanical separation methods such as sedimentation, centrifugation, filtration, etc., to separate the solid matter. Additional diatomaceous-earth filtration treatment of pre-treated liquid from prior steps may be used to remove color bodies.

Example A3. Preservation Technics For CFSE

For the case of liquid-fluid aqueous extract solutions (from Example A2 above) which must be stored for extended periods in a bulk tank (to prevent growth of microbes) by either:

(a) adding a small amount (0.001 to 1.0 wt. %) of one or more chemical preservatives such as methyl and propyl paraben, or blends thereof, or (b) dewatering the active CFSE to a dry-powder form by vacuum evaporation, spray drying, freeze drying, Example A4. Air Drying and Storage-Preparation Process for Symphytum Plant Elements This is a process for preparing harvested Symphytum plant elements to be stored for extraction at a future time which includes the steps of:

(a) removing water from the plant elements to reduce their water content to 10 wt. % or less, by a flow of heated, dried air (50% RH max, max. air temperature below 65 deg. C., times may range from 10 to 100 hours depending upon the actual RH and flow rate) through a loose bed or across the surface, starting at step (d) of Example A1. above, and (b) charging the resulting dried plant elements into sealed, radiation-impervious containers along with an inert, air-excluding fluid atmosphere such as volatile alcohol or fluorocarbon which prevents chemical degradation of the active constituents.

Group B. Examples of different topical O/W-emulsion dermatologic formulations which contain CFSE, e.g., ointment, salve, lotion, cream, spray, infusion fluids, etc. In these examples, the CF Symphytum Extract is dissolved into the indicated quantity of carrier solution or base such as water, glycerol, propylene glycol.

Example B1. Water-Based CF Symphytum Extract Solution

| A. Water Phase | |
|---|---|
| CFSE | 2-20 grams |
| distilled water | 1000 grams |
| methyl paraben | 1 gram |
| propyl paraben | 0.5 gram |

Example B2. DH100 formulation

| | | % by weight |
|---|---|---|
| A. Water Phase | | |
| methyl paraben | 17.0 grams | 0.102% |
| propyl paraben | 8.5 grams | 0.051% |
| triethanolamine | 903. grams | 5.433% |
| allantoin | 152. grams | 0.914% |
| deionized or distilled water | 9375. grams | 56.402% |
| CF Symphytum ext. in glycerol | 2340. grams | 14.078% |
| B. Oil Phase | | |
| stearic acid | 600. grams | 3.611% |
| glyceryl monostearate | 1575. grams | 9.476% |
| cetyl alcohol | 840. grams | 5.054% |
| olive oils | 320. grams | 1.925% |
| castor oil | 230. grams | 1.384% |
| jojoba oil | 230. grams | 1.384% |
| myrrh oil | 30. grams | 0.180% |
| peppermint oil | 1.25 grams | 0.008% |
| | 16,621.75 grams | |

C. Heat both phases to 73° C. pour A into B while mixing to form a W/O/W emulsion. Continue mixing until the temperature of the mixture is 65° C. or less.

Example B3. SCP100 formulation

| | | % by weight |
|---|---|---|
| A. Water Phase | | |
| CF Symphytum Ext. in glycerol, or deionized or distilled water | 624. grams | 13.675% |
| | 3.250. grams | 71.225% |
| allantoin | 50. grams | 1.096% |
| methyl paraben | 5. grams | .111% |
| propyl paraben | 2.5 grams | .055% |
| diazolidinyl urea | 10.5 grams | .230% |
| B. Oil Phase | | |
| stearic acid | 144. grams | 3.156% |
| cetyl | 208. grams | 4.558% |
| olive oil | 54. grams | 1.183% |
| castor oil | 34. grams | .745% |
| jojoba oil | 34. grams | .745% |
| myrrh oil | 10. grams | .219% |
| polyoxyethylene (2) stearyl ether | 34. grams | .745% |
| polyoxyethylene 21 stearyl ether | 103. grams | 2.257% |
| | 4,653. grams | |

C. Heat both phases to 73° C. Pour A into B while mixing to form a W/O/W emulsion. Continue mixing until the -continued

| | % by weight |
|---|---|
| temperature of the mixture is 50° C. or less. | |

Example B4. DC102 formulation

| A. Water Phase | | | % by weight |
|---|---|---|---|
| methyl paraben | 1. | grams | .100% |
| propyl paraben | 0.2 | grams | .020% |
| CF Symphytum Ext. in glycerol | 150. | grams | 14.851% |
| allantoin | 10. | grams | .990% |
| sodium ascorbate | 10. | grams | .990% |
| polysorbate 80 | 10. | grams | .990% |
| deionized water | 576. | grams | 57.030% |
| B. Oil Phase | | | |
| stearic acid | 40. | grams | 3.960% |
| glyceryl monostearate | 105. | grams | 10.396% |
| steryl alcohol | 56. | grams | 5.544% |
| liquid petrolatum | 52. | grams | 5.149% |
| | 1,010. | grams | |

C. Heat both phases to 73° C. While mixing add B into A to form a W/O/W emulsion. Continue mixing until the temperature of the mixture is 50° C. or less.

Example B5. DC139 formulation

| A. Water Phase | | | % by weight |
|---|---|---|---|
| methyl paraben | 20. | grams | .100% |
| propyl paraben | 4. | grams | .020% |
| CF Symphytum Ext. in propylene glycol | 2953. | grams | 14.794% |
| allantoin | 204. | grams | 1.022% |
| polysorbate 80 | 200. | grams | 1.002% |
| deionized or distilled water | 11,520. | grams | 57.713% |
| B. Oil Phase | | | |
| stearic acid | 800. | grams | 4.008% |
| glyceryl monostearate | 2100. | grams | 10.521% |
| stearyl alcohol | 1120. | grams | 5.611% |
| liquid petrolatum | 1040. | grams | 5.210% |
| | 19,961. | grams | |

C. Heat both phases to 73° C. Pour B into A while mixing to form an O/W emulsion. Continue mixing until the temperature of the mixture is 50° C. or less.

Example B6. SCP293 formulation

| A. Water Phase | | | % by weight |
|---|---|---|---|
| methyl paraben | 20. | grams | .097% |
| propyl paraben | 12. | grams | .058% |
| CF Symphytum Ext. in glycerol | 3084. | grams | 14.980% |
| allantoin | 202. | grams | .980% |
| triethanolamine | 400. | grams | 1.900% |
| distilled water | 15,000. | grams | 72.880% |
| B. Oil Phase | | | |
| stearic acid | 268. | grams | 1.300% |
| glyceryl monostearate | 700. | grams | 3.400% |
| cetyl alcohol | 374. | grams | 1.820% |
| olive oil | 214. | grams | 1.040% |
| castor oil | 168. | grams | .820% |
| jojoba oil | 100. | grams | .490% |
| myrrh oil | 40. | grams | .190% |
| peppermint oil | 1.25 | grams | .006% |

C. Heat both phases to 73° deg. C. Pour A into B while agitating to form a water-in-O/W emulsion. Continue mixing until the temperature of the mixture drops below 50° C.

From 0.5–5.0 wt. % of *Melaleuca uncinata* oil (frequently called Tea Tree oil) can be added to any of the examples (B1 to B6 above) for the purpose of inhibition of fungal growth at a dermal application site e.g., athlete's foot treatment, applied between toes.

Group C. Examples of non-emulsion CF Symphytum Extract pharmaceutical formulations i.e., single-phase solutions, vesicles, liposome, micelles, aerosols, tablets, microcapsules, caplets, injectable fluids, transdermal delivery patch/device, etc.

Example C1. Isotonic Liposome Formulation LS141

Isotonic liposomes are desirable for application of CFSE to sensitive tissue, wounds, mucous membrane, or as an ingredient in an injectable, implantable, or inhalable preparation.

Use water phase from example B1 above; adjust the solution osmolality to physiologic range (250–350 mOsm/kg) by the addition of concentrates containing physiologic salts, glucose, etc.. Form the liposome by adding the solution to a dry film of lipid such as lecithin or cholesterol; use sonication if needed.

Example C2. Aerosol Formulations A293

Aerosol formulations are of particular value in application of CFSE to hairy areas of human or animal bodies. In order to prepare lyophilized solid forms of CF Symphytum Extract, the extraction stage would be done with a minimal amount of water or alcohol to facilitate dewatering by evaporation, spray drying or freeze drying. Solid aerosols can be used with pressurized propellants in devices which meter and disperse the dry particles into a gas-type aerosol which may be inhaled for treatment of nasal membranes.

For liquid dispersions, a known vesicle- or emulsion-stabilizing agent is dissolved into a volatile, biocompatible propellant-solvent such as R-12 fluorocarbon. The resulting fluid is packaged into a pressurized propellant spray device to facilitate direct external application to scalp, skin or mucosal tissue.

Example C3. Transdermal/Transmucosal formulation A291

CFSE such as Example B1 above are blended with known skin adhesive compounds to produce a diffusion-controlled drug delivery reservoir. Additional selected therapeutic agents may also be added for specific functions such as: (a) low levels of DMSO for enhancing the rate of absorption of the Symphytum healing agents into the skin, or (b) or synergistically increasing the healing properties of the CFSE e.g., D-alphatocopherol in transmucosal adhesive devices.

Example C4. Microencapsulated formulations M 17–19

Dry-powder forms of CFSE such as Example B1 dewatered by the process of Example A3(b), are encapsulated as microspheres (0.01 to 1.0 mm diam.) within thin, polymeric membranes using known spray-drying technics. These forms can be used for controlled release in transdermal, transmucosal, enteral, or parenteral preparations.

D. Examples of selected methods of using various formulations of CFSE (see Groups A., B. and C. above).

Example D1. Adhesive patch for delivering controlled amounts/rates (skin, mucous membrane). Aqueous emulsion CFSE is added during the preparation of a known hydrogel adhesive for use on human skin so that the resulting cast layer or film serves as a reservoir matrix and a diffusion-controlled delivery means for the active agents of the extract.

Example D2. Conductive electrode adhesive formulations with CF Symphytum Extract (TENS, long-term EKG monitoring, iontophoresis, etc.).

One frequent complication of transdermal electro-stimulation for the relief of pain is a skin rash which develops in the tissue layers subject to the effects of the material, current pulses and the conductive electrode gels/creams. Similarly, electrocardiac monitoring apparatus, such as a Holter monitor, and iontophoresis devices also can produce painful skin rashes. CFSE are blended into the conductive paste or the skin adhesive to alleviate these conditions (see Example D1 above).

Example D3. Impregnated tampon for delivering selected CF Symphytum Extract dosage to intravaginal membranes. An emulsion formulation such as Example B2 with Tea-Tree oil addition is used. Alternatively, a liposomal formulation such as Example C1 is used; by the addition of a binding ligand or antibody specific for the critical fungal vector e.g., *candida albicans,* to the vesicle surface, the vesicles is targeted directly toward the infectious process.

Example D4. Microencapsulated or dry-powder aerosol forms of CFSE such as Example C2. is administered by known metering aerosol devices for the treatment of throat or nasal irritations/inflamations which may occur in accident situations involving poison-gas attacks, fires, explosions, and exposures to irritating chemical vapors/mists.

Example D5. Liquid aerosol or liposome forms of CFSE is administered by a spray dispenser for scalp treatment e.g., sunburn or hair-loss. For enhanced hair-growth stimulation, CFSE are blended into known compounds. Similarly, for the treatment of aging and skin wrinkles, CFSE are blended with compounds which are known to improve the elastic tone and thickness of the skin layer structure; for such conditions, a known acoustic or ultrasonic device is used along with the application to accelerate absorption into the skin.

Example D6. Wax-type suppository for colitis treat. CFSE are blended into a known suppository vehicle prior to forming the suppository device.

Example D7. CFSE for Treating Skin Conditions Related to HIV Virus Study 2303—10 patients, formulation of Example B2 used for about 6 months for eczema, folliculitis, and dry itchy skin.

RESULTS: About half the patients indicated symptomatic relief and requested additional supplies of the formulation for continuing use.

Example D8. CFSE for Treating Skin Lesions Related to Kaposi's Sarcoma (KS) in HIV Population Study 1011—Small-group test of formulation of Example B2. Used for KS skin wounds/eruptions.

RESULTS: Formulation cleared up most skin problems and closed spots.

Example D9. CFSE for Skin Problems In Diabetes Population Study 805. Group of 98 diabetes patients used formulation in Example B6 over a period of about 30 days for treatment of dry skin and other diabetes-related skin complications. Written evaluation instrument given to each participant to mail in at the completion of the test period. For the preliminary report, the data on 39 questionnaire responses was analyzed.

RESULTS: About 87% of the respondents indicated that the formulation was satisfactory or very satisfactory for the relief of dry-skin complications.

EXAMPLE E. Therapeutic Validation of CFTE in Mammals

Known in-vivo testing methods can be used to evaluate the cytotoxic and cell-proliferation-inhibition effectiveness of CFTE, e.g., subcutaneous injections, murine animal model, daily dose range 0.01 to 1 ml/kg of active agents based upon total body weight or the specific organ weight. In-vitro testing methods for CFTE include inhibition of murine monocyte activation. It is believed that the cytocidal mechanism is similar to that of other alkaloids, i.e., inhibition of the formation of microtubules in tumor cells.

On the basis of confirmation by such lab tests and animal studies, it is expected that CFTE formulations are useful in treating mammalian adenocarcinomas and tumors of specific organs such as the kidney, liver, pancreas, breast, colon, prostate and esophagus. Various sterile-fluid formulations/vehicles/excipients may be used for parenteral administration of CFTE, including single-phase solutions, emulsions, suspensions, foams, or liposomes. Using known methods for controlled release or volume blending, CFTE formulations can be added to IV solutions. It is believed that CFTE formulations also potentiate or enhance the mammalian immune response through various interactions including inhibition of protein kinase C.

EXAMPLE F. Therapeutic Validation of CFAE in Mammals

On the basis of confirming lab tests and animal studies, it is expected that CFAE formulations are useful in many topical compositions for treating skin dryness, irritation, burns, abrasions sensitization to skin electrodes and other conditions. CFAE may be used with significant benefit along with CFSE in many of the topical formulations.

EXAMPLE G. Additional Therapeutic Formulations of CFSE, CFTE, and CFAE For Mammals.

CFSE, CFTE, and CFAE medicaments described above may be further modified by the addition of one or more of the following general types of agents: antibiotics, analgesics, enzymes (such as elastase, collagenase, lipase), steroids (such as hydrocortisone), vitamins (such as A, B, C, E), hormones, biotin cofactors, emollients (such as lanolin), immunoglobulins, vaccines and other immumologic agents.

The preceeding examples of this invention can be repeated with similar success by substituting the generically or specifically described reagents for those used in the examples.

From the examples presented and previous descriptions, one skilled in the art can easily ascertain the essential characteristics of this invention, and without departing from the spirit and scope thereof, can make various changes and modifications of the invention to adapt it to various starting materials, body-healing usages and administration forms/conditions.

We claim:

1. A process for preparation of Concentrated Fluid Symphytum Extracts, CFSE, which comprises the steps of:

selecting live, healthy plants of single or mixed wild or non-wild taxonomically-classified plant species comprising

*S. officinale, S. asperum, S. armeniacum, S. tauricum, S. sylvaticum, S. peregrinum, S. anatolicum, S. icaricum, S. orientale, S. kurdicum, S. pseudobutbosum, S. uplandicum, S. circinale, S. ottomanum, S. icaricum, S. brachycalyx, S. aintabicum, S. longisetum, S. bornmuelleri, S. tuberosum, S. bulbosum, S. ibericum,* or *S. longipetiolatum* ;

harvesting whole parts of said plant species comprising one or more of roots, stems, leaves, anthers, buds, and blooms;

charging said whole harvested parts immediately into protective, tightly-closed chambers, which are sunlight-opaque, and which provides a protective environment to prevent moisture evaporation and light-activated chemical, biological processes;

removing said charged whole parts from said protective chamber and comminuting them immediately within a protective environment to a length or thickness dimension of approx. 1 mm;

charging said comminuted parts within a time period of approximately 1-2 hours into a closed, extraction apparatus adapted to provide controlled ranges of internal pressure, temperature and a forced-convection-contact-velocity differential between said comminuted parts and an extraction fluid for an extended diffusion time, charging an extraction fluid into said extraction apparatus wherein said extraction fluid is a chemical compound, a single phase or multiple phases, a vapor or liquid solution, or a suspension, and the mass ratio of said extraction fluid to said comminuted plant parts lies in the range 0,01 to 10000 wherein said extraction fluid comprises single-or two-phase water, single- or two-phase water solutions with one or more biocompatible solutes, two-phase fluids with a liquid with equilibrium vapor phase, multi-phase, multi-component biocompatible fluid solutions with one or more dispersed liquid phases, and an equilibrium vapor phase, or multi-phase, multi-component biocompatible fluid solutions with one or more dispersed liquid phases, and an equilibrium vapor phase containing dispersed droplets, particles, or vesicles;

extracting, by diffusional transfer, biologically active species into said extraction fluid from said comminuted plant parts in said extraction apparatus for a total diffusion time in the range 1-200 hours while forced-convection-contact-velocity differential is maintained within the range 0,5-3 meter/sec; and internal temperature is in the range 20-380 deg. K. and an absolute internal pressure is in the range 1-5000 kPa;

separating solid plant residues from supernatant Concentrated Fluid Symphytum Extract by physical means comprising solvent extraction, sedimentation, coagulation, distillation, centrifugation or filtration through microporous, adsorbent media, wherein said extraction fluid consists of 1,2 propanediol-free liquid or vapor phases.

2. The process for preparation of CFSE of claim 1 wherein said selection step comprises selecting mature plants of single or mixed wild or non-wild taxonomically-classified plant species which are at peri-bloom stage, free from parasite infestation and plant disease, free from gross external chemical contamination, free from residues of fertilizers/horticultural compounds, free from mechanical contamination comprising;

S. officinale, S. asperum, S. armeniacum, S. tauricum, S. sylvaticum, S. peregrinum, S. anatolicum, S. icaricum, S. orientale, S. kurdicum, S. pseudobulbosum, S. uplandicum, S. circinale, S. ottomanum, S. icaricum, S. brachycalyx, S. aintabicum, S. longisetum, S. bornmuelleri, S. tuberosum, S. bulbosum, S. ibericum, or S. longipetiolatum and said harvesting step is preceeded by a intermediate step comprising treating and conditioning said selected plants at a time just prior to harvest with fluids and sprayed agents to kill and wash off mechanical surface contaminants including adventitious bacteria, airborne particulate contaminants, and undesired residues of horticultural chemicals wherein said fluids and sprayed treating agents comprise aqueous solutions, or aqueous solutions-suspensions containing live bacteria and necessary support agents including surfactants, nutrients, preservatives, antioxidants necessary for supporting said live bacteria;

3. The process of claim 1, wherein said extraction fluid is a quantity of liquid water solution which amounts 100-1000 times the mass of said comminuted plant matter and which is injected at a temperature of 50-70 deg. C. at a pressure of 90-110 kPa as a spray with a average forced-convection-contact-velocity-differential of 0.5-3 meter/sec.

4. The process of claim 1, wherein the extraction fluid is a liquid water solution containing up to 0.01 wt. % of a known pharmaceutical surfactant and the total diffusion time consists of a single cycle of 100-200 hours duration at 50-70 deg. C., 90-110 kPa, and a forced convection contact velocity differential of 0.1-3 meter/sec.

5. The process of claim 1, wherein the extraction fluid is liquid water, the total diffusion time consists of a first cycle of 1-20 hours duration at 30-90 kPa, 50-70 deg. C., and a forced convection contact velocity of 1-5 meter/sec followed by a second cycle of 180-200 hours duration at 100-200 kPa, 40-60 deg. C., and a forced convection contact velocity differential of 0.5-5 meter/sec.

* * * * *